United States Patent
Sakata et al.

(10) Patent No.: US 9,492,424 B2
(45) Date of Patent: Nov. 15, 2016

(54) MUSCLE ATROPHY INHIBITOR

(71) Applicant: MORINAGA MILK INDUSTRY CO., LTD., Tokyo (JP)

(72) Inventors: Yasuyuki Sakata, Kanagawa (JP); Hirohiko Nakamura, Kanagawa (JP); Kazutaka Oshio, Kanagawa (JP)

(73) Assignee: MORINAGA MILK INDUSTRY CO., LTD., Tokyo (JP)

( * ) Notice: Subject to any disclaimer, the term of this patent is extended or adjusted under 35 U.S.C. 154(b) by 0 days.

(21) Appl. No.: 14/365,796

(22) PCT Filed: Dec. 26, 2012

(86) PCT No.: PCT/JP2012/083719
§ 371 (c)(1),
(2) Date: Jun. 16, 2014

(87) PCT Pub. No.: WO2013/099982
PCT Pub. Date: Jul. 4, 2013

(65) Prior Publication Data
US 2014/0356462 A1 Dec. 4, 2014

(30) Foreign Application Priority Data
Dec. 26, 2011 (JP) ................. 2011-283004

(51) Int. Cl.
*A01N 65/00* (2009.01)
*A61K 31/353* (2006.01)
*A61K 31/352* (2006.01)
*A61K 36/752* (2006.01)
*A61K 9/00* (2006.01)
*A61K 47/48* (2006.01)
*C08B 37/16* (2006.01)
*C08L 5/16* (2006.01)
*A23L 2/52* (2006.01)

(52) U.S. Cl.
CPC ............ *A61K 31/353* (2013.01); *A23L 2/52* (2013.01); *A23L 33/105* (2016.08); *A61K 9/0056* (2013.01); *A61K 9/0095* (2013.01); *A61K 31/352* (2013.01); *A61K 36/752* (2013.01); *A61K 47/48969* (2013.01); *C08B 37/0015* (2013.01); *C08L 5/16* (2013.01); *Y02P 20/544* (2015.11)

(58) Field of Classification Search
CPC .................................................. A61K 36/00
USPC ........................................................ 424/725
See application file for complete search history.

(56) References Cited

U.S. PATENT DOCUMENTS

2002/0040052 A1 4/2002 Ito et al.
2007/0213282 A1 9/2007 Sasaki

FOREIGN PATENT DOCUMENTS

| JP | H 06-72870 A | 3/1994 |
|---|---|---|
| JP | 2001-240539 A | 9/2001 |
| JP | 2002-060340 A | 2/2002 |
| JP | 2004-083417 A | 3/2004 |
| JP | 2006-328031 A | 12/2006 |
| JP | 2007-145809 A | 6/2007 |
| JP | 2008-013473 A | 1/2008 |
| JP | 2008-156294 A | 7/2008 |
| JP | 2008-179620 A | 8/2008 |
| JP | 2009-007313 A | 1/2009 |
| JP | 2009-256282 A | 11/2009 |
| JP | 2009-256283 A | 11/2009 |
| JP | 2010-047529 A | 3/2010 |
| JP | 4633897 B2 | 11/2010 |
| JP | 2011-037798 A | 2/2011 |
| WO | WO 2004/047766 A2 | 6/2004 |
| WO | WO 2006/049234 A1 | 5/2006 |
| WO | WO 2007/024982 A2 | 3/2007 |
| WO | WO 2009/083612 A2 | 7/2009 |
| WO | WO 2010/085788 A1 | 7/2010 |

OTHER PUBLICATIONS

Miyaki et al., Nippon Shokuhin Kagaku Kogaku; Kaishi vol. No. 56; Issue No. 4; Year: 2009 pp. 193-199.*
Akachi et al., J. Nutr. Sci. Vitaminol, 56, 6-67, 2010.*
What is sarcopenia ?, 1 page, 2015.*
Office Action issued in corresponding Korean Patent Application No. 10-2014-7020695, on May 31, 2016.
Kim et al., "Aqueous Solubility Enhancement of Some Flavones by Complexation with Cyclodextrins," *Bull. Korean Chem. Soc.*, vol. 29(3), pp. 590-594 (2008).
Altun et al., "Muscle Wasting in Aged, Sarcopenic Rats is Associated with Enhanced Activity of the Ubiquitin Proteasome Pathway," *The Journal of Biological Chemistry*, vol. 285(51), pp. 39597-39608 (2010).
Doherty, "Invited Review: Aging and sarcopenia," *Journal of Applied Physiology*, vol. 95(4), pp. 1717-1727 (2003).
Uezumi et al., "Mechanism and therapeutic application against skeletal muscle atrophy in aging and diseases," *Biomedical Gerontology*, vol. 34(4), pp. 5-11 (2010).

(Continued)

Primary Examiner — Michael Meller
(74) Attorney, Agent, or Firm — Knobbe, Martens, Olson & Bear, LLP

(57) ABSTRACT

An extract of *Citrus depressa*, preferably an organic solvent extract of a fruit and/or leaf of *Citrus depressa*, a supercritical extract of a fruit and/or leaf of *Citrus depressa*, or a subcritical extract of a fruit and/or leaf of *Citrus depressa*, containing 0.3 mass % or more of a polymethoxyflavonoid in terms of solid matter, for example, 0.2 mass % or more of nobiletin and/or 0.1 mass % or more of tangeretin in terms of solid matter, or a polymethoxyflavonoid, such as nobiletin and tangeretin, is used as an active ingredient of a muscle atrophy inhibitor.

13 Claims, 2 Drawing Sheets

(56) References Cited

OTHER PUBLICATIONS

Extended European Search Report issued in corresponding European Patent Application No. 12861908.7, dated Aug. 7, 2015.
International Search Report for International Application No. PCT/JP2012/083719, mailed on Feb. 5, 2013.
Jackson et al., "Mediation of endogenous antioxidant enzymes and apoptotic signaling by resveratrol following muscle disuse in the gastroonemius muscles of young and old rats," *Am J Physiol Regul Integr Comp Physiol*, vol. 299, pp. R1572-R1581 (2010).
Koga et al., "Comparative Study on Nobiletin Metabolism with Liver Microsomes from Rats, Guinea Pigs and Hamsters and Rat Cytochrome P450," *Biol. Pharm. Bull.*, vol. 30(12), pp. 2317-2323 (2007).
Lee et al., "Extraction of nobiletin and tangeretin from *Citrus depressa* Hayata by supercritical carbon dioxide with ethanol as modifier," *Industrial Crops and Products*, vol. 31, pp. 59-64 (2010).
Menezes et al., "Creatine supplementation attenuates corticosteroid-induced muscle wasting and impairment of exercise performance in rats," *J Appl Phsyiol*, vol. 102, pp. 698-703 (2007).
Ohtsuka et al., "Vitamin E Reduces Glucocorticoid-Induced Oxidative Stress in Rat Skeletal Muscle," *J. Nutr. Sci. Vitaminol.*, vol. 44, pp. 779-786 (1998).
Takenaka et al., "Effective Recovery of Polymethoxyflavanoids by Multi-stage Extraction of *Citrus depressa*," *Food Sci. Technol. Res.*, vol. 16(6), pp. 627-630 (2010).
Yamamoto et al., "Branched-chain Amino Acids Protect Against Dexamethasone-induced Soleus Muscle Atrophy in Rats," *Muscle & Nerve*, vol. 41, pp. 819-827 (Jun. 2010).
You et al., "Dietary fish oil alleviates soleus atrophy during immobilization in association with Akt signaling to p70s6k and E3 ubiquitin ligases in rats," *Appl. Physiol. Nutr. Metab.*, vol. 35, pp. 310-318 (2010).
Office Action issued in corresponding Korean Patent Application No. 10-2014-7020695, dated Nov. 20, 2015.

* cited by examiner

MUSCLE ATROPHY INHIBITOR

CROSS-REFERENCE TO RELATED APPLICATIONS

This application is the U.S. National Phase under 35 U.S.C. §371 of International Application PCT/JP2012/083719, filed Dec. 26, 2012, which was published in a non-English language, which claims priority to JP 2011283004, filed Dec. 26, 2011.

TECHNICAL FIELD

The present invention relates to a muscle atrophy inhibitor. A muscle atrophy inhibitor can be used as a drug, food, and feed.

BACKGROUND ART

Muscle atrophy refers to a state that muscle mass decreases due to reduction of muscle fiber number and reduction of muscle fiber volume, and is usually accompanied by decreased muscle force. Although appropriate exercise is effective for prophylaxis or improvement of muscle atrophy, recovery by exercise is difficult for sick persons and old people. Therefore, development of a drug or food effective for suppression or improvement of muscle atrophy is expected.

As techniques for inhibiting muscle atrophy using ingredients contained in plants, there are known muscle atrophy inhibitors containing Araliaceae ginseng radix (Patent document 1), α-glucosylated hesperidin (Patent document 2), or stigmasterol (Patent document 3) as an active ingredient, and an inhibitor of muscle fiber type shift containing a fruit-derived polyphenol (Patent document 4) as an active ingredient.

Further, as techniques for improving muscle function or suppressing reduction of muscle function, there are known a muscle function reduction inhibitor containing catechins as an active ingredient (Patent document 5), a endurance improver containing resveratrol and/or grape leaf extract as an active ingredient (Patent document 6), an anti-amyotrophic lateral sclerosis (ALS) agent containing rosmarinic acid or carnosic acid as an active ingredient (Patent document 7), and an anti-ALS agent containing a rosemary extract or sage extract as an active ingredient (Patent document 8).

As a plant-derived health food raw material, extract of *Citrus depressa* attracts attention. Various efficacies of polymethoxyflavonoids such as nobiletin and tangeretin contained in extract of *Citrus depressa* have been found to date. For example, it is reported that nobiletin has a neurite outgrowth action (Patent document 9), anti-hypertension and anti-cancer actions (Patent document 10), heart disease preventing and treating actions (Patent document 11), anti-ulcer action (Patent document 12), and so forth. Further, it has been reported that polymethoxyflavonoids such as tangeretin and nobiletin have a neovascularization suppressing action (Patent document 13). Furthermore, it is known that flavonoids contained in *Citrus* species such as *Citrus depressa* have a blood pressure elevation suppressing action (Patent document 14).

Further, the aforementioned inhibitor of muscle fiber type shift (Patent document 4) uses a polyphenol such as, specifically, procyanidin contained in fruits of Rosaceae plants such as apple, as an active ingredient.

However, such flavonoids as mentioned above are scarcely contained in fruit juice, but are mostly contained in pericarps. Therefore, only by squeezing fruits, these flavonoids are obtained only at a low content.

Polymethoxyflavonoids constitute one class of flavonoid, have a special structure in which a plurality of phenolic hydroxyl groups are methylated, and are mainly contained in *Citrus* species. It has also been reported that polymethoxyflavonoids such as nobiletin or tangeretin are metabolized in the liver after intake, and the generated metabolites enhance anti-inflammatory action. For example, methoxy groups of nobiletin are converted into hydroxyl groups by metabolism in the liver of rat, and nobiletin derivatives having 4'-OH, 7-OH, 6-OH, 3',4'-diOH, 6,7-diOH or the like are generated as metabolites. Further, it has been reported that, from tangeretin, tangeretin derivatives having 4'-OH, 3',4'-diOH, 7,4'-diOH, 6,7-diOH or the like are generated as metabolites (Non-patent document 1).

Although several plant-derived ingredients having a muscle atrophy inhibition action are known as described above, it is not known that extract of *Citrus depressa* or a polymethoxyflavonoid such as nobiletin and tangeretin has a muscle atrophy inhibition action.

As a method for preparing a muscle atrophy model for evaluating food materials, a method using a glucocorticoid, and a method using hindlimb immobilization or unloading are known. There have been reported that effect of a branched chain amino acid on cross-sectional areas of muscle fibers etc. (Non-patent document 2), and effects of creatine (Non-patent document 3) and vitamin E (Non-patent document 4) on muscle weight were evaluated by using a muscle atrophy model derived with a glucocorticoid. Further, there have also been reported that effects of resveratrol (Non-patent document 5) and fish oil (Non-patent document 6) on muscle weight were evaluated by using a muscle atrophy model prepared by using hindlimb immobilization or unloading.

However, there is no report concerning evaluation of muscle atrophy inhibition action of extract of *Citrus depressa* or ingredients thereof with these models or others.

PRIOR ART REFERENCES

Patent Documents

Patent document 1: Japanese Patent Laid-open (Kokai) No. 2008-179620
Patent document 2: Japanese Patent Laid-open No. 2009-7313
Patent document 3: Japanese Patent Laid-open No. 2010-47529
Patent document 4: Japanese Patent Laid-open No. 2006-328031
Patent document 5: Japanese Patent Laid-open No. 2008-13473
Patent document 6: Japanese Patent Laid-open No. 2007-145809
Patent document 7: Japanese Patent Laid-open No. 2009-256282
Patent document 8: Japanese Patent Laid-open No. 2009-256283
Patent document 9: Japanese Patent No. 4633897
Patent document 10: International Patent Publication WO2006/49234
Patent document 11: Japanese Patent Laid-open No. 2011-37798

Patent document 12: Japanese Patent Laid-open No. 6-72870
Patent document 13: Japanese Patent Laid-open No. 2004-83417
Patent document 14: Japanese Patent Laid-open No. 2001-240539

Non-Patent Documents

Non-patent document 1: Koga, N. et al., Biol. Pharm. Bull. 30(12), 2317-2323, 2007
Non-patent document 2: Yamamoto, D. et al., Muscle & Nerve, 41:819-827, 2010
Non-patent document 3: Menezes, L.G. et al., J. Appl. Physiol., 102:698-703, 2007
Non-patent document 4: Ohtsuka, A. et al., J. Nutr. Sci. Vitaminol., 44, 779-786, 1998
Non-patent document 5: Jackson, J.R. et al., Am. J. Physiol. Integr. Comp. Physiol., 299:R1572-R1581, 2010
Non-patent document 6: You, J.-S. et al., Appl. Physiol. Nutr. Metab., 35:310-318, 2010

SUMMARY OF THE INVENTION

Object to be Achieved by the Invention

An object of the present invention is to provide a muscle atrophy inhibitor that can be safely ingested, and a food or drink containing it.

Means for Achieving the Object

The inventors of the present invention conducted various researches in order to achieve the aforementioned object. As a result, they found that an extract of Citrus depressa or an ingredient thereof had a superior muscle atrophy inhibition action, and accomplished the present invention.

The present invention thus provides the following.

[1] A muscle atrophy inhibitor comprising an extract of *Citrus depressa* as an active ingredient.

[2] The muscle atrophy inhibitor according to [1], wherein the extract of *Citrus depressa* is an organic solvent extract of a fruit and/or leaf of *Citrus depressa*.

[3] The muscle atrophy inhibitor according to [1], wherein the extract of *Citrus depressa* is a supercritical extract or subcritical extract of a fruit and/or leaf of *Citrus depressa*.

[4] The muscle atrophy inhibitor according to [2], wherein the organic solvent is selected from the group consisting of methanol, ethanol, propanol, butanol, ethyl acetate, acetone, hexane, chloroform, diethyl ether, and these organic solvents comprising water.

[5] The muscle atrophy inhibitor according to [4], wherein the organic solvent is ethanol or water-comprising ethanol.

[6] The muscle atrophy inhibitor according to [1], wherein the extract of *Citrus depressa comprises polymethoxyflavonoid*.

[7] The muscle atrophy inhibitor according to [6], wherein the extract of *Citrus depressa* comprises 0.3 mass % or more of a polymethoxyflavonoid in terms of solid matter.

[8] The muscle atrophy inhibitor according to [6], wherein the polymethoxyflavonoid comprises nobiletin and/or tangeretin.

[9] The muscle atrophy inhibitor according to [8] wherein the extract of Citrus depressa comprises 0.2 mass % or more of nobiletin and/or 0.1 mass % or more of tangeretin in terms of solid matter.

[10] The muscle atrophy inhibitor according to [6], which further comprises a clathrating agent for making the polymethoxyflavonoid water-soluble.

[11] The muscle atrophy inhibitor according to [10], wherein the clathrating nt is cyclodextrin, and content thereof is 0.1 to 95 mass % based on the total mass of solid matter of the extract of Citrus depressa and the cyclodextrin.

[12] A muscle atrophy inhibitor comprising a polymethoxyflavonoid as an active ingredient.

[13] The muscle atrophy inhibitor according to [12] wherein the polymethoxyflavonoid comprises nobiletin and/or tangeretin.

[14] A food or drink comprising 0.3 mass % or more of the muscle atrophy inhibitor according to [6] as polymethoxyflavonoid content in terms of solid matter.

[15] A food or drink comprising 0.2 mass % or more of the muscle atrophy inhibitor according to [13] as nobiletin content in terms of solid matter.

[16] A food or drink comprising 0.1 mass % or more of the muscle atrophy inhibitor according to [13] as content in terms of solid matter.

[17] An extract of Citrus depressa to be used for inhibiting muscle atrophy

[18] A polymethoxyflavonoid to be used for inhibiting muscle atrophy.

[19] A method for inhibiting muscle atrophy, which comprises administering an extract of *Citrus depressa* to a mammal.

[20] The method for inhibiting muscle atrophy according to [19] wherein the extract of *Citrus depressa* comprises polymethoxyflavonoid.

[21] The method for inhibiting muscle atrophy according to [19], wherein the extract of *Citrus depressa* comprises 0.3 mass % or more of a polymethoxyflavonoid in terms of solid matter.

[22] The method for inhibiting muscle atrophy according to [20], wherein the polymethoxyflavonoid comprises nobiletin and/or tangeretin.

[23] The method for inhibiting muscle atrophy according to [22], wherein the extract of *Citrus depressa* comprises 0.2 mass % or more of nobiletin and/or 0.1 mass % or more of tangeretin in terms of solid matter.

[24] A method for inhibiting muscle atrophy, which comprises administering polymethoxyflavonoid to a mammal.

[25] The method for inhibiting muscle atrophy according to [24], wherein the polymethoxyflavonoid comprises nobiletin and/or tangeretin.

EMBODIMENTS FOR CARRYING OUT THE INVENTION

Figure 1:
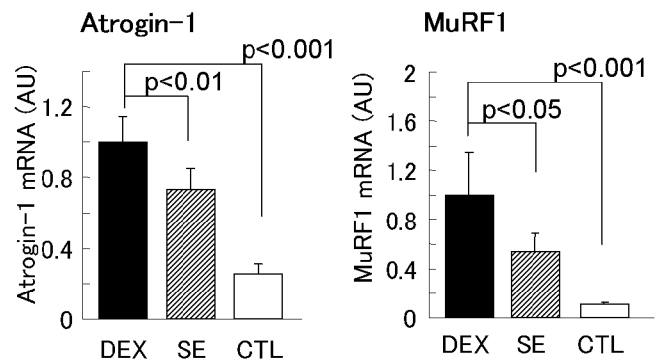
FIG. 1 includes graphs showing change of expression of muscle atrophy-related genes provided by administration of an extract of *Citrus depressa*.
CTL: Dexamethasone non-administration group
DEX: Dexamethasone administration group
SE: Dexamethasone and extract of *Citrus depressa* (shiiku-washa extract) administration group
FIG. 2 includes graphs showing change of expression of muscle atrophy-related genes provided by administration of polymethoxyflavonoid (PMF), nobiletin (NOB), and tangeretin (TAN).
CTL: Dexamethasone non-administration group
DEX: Dexamethasone administration group
PMF: Dexamethasone and polymethoxyflavonoid administration group
NOB: Dexamethasone and nobiletin administration group
TAN: Dexamethasone and tangeretin administration group

Hereafter, preferred embodiments of the present invention will be explained in detail. However, the present invention is not limited to the following preferred embodiments, but can be freely modified within the scope of the present invention.

The muscle atrophy inhibitor of the present invention contains an extract of *Citrus depressa* or a polymethoxyflavonoid as an active ingredient. Examples of the polymethoxyflavonoid include polymethoxyflavonoids contained in *Citrus depressa* or an extract thereof. The polymethoxyflavonoids contained in *Citrus depressa* or an extract thereof have a structure generally represented by the following formula, and specific examples include nobiletin, tangeretin, 5-demetylated nobiletin, 8-demethoxylated nobiletin (sinensetin), 6-demethoxylated tangeretin, 6-demethoxylated nobiletin, citromitin, 5,6,7,8,4-pentamethoxyflavanone, and so forth. Among these, nobiletin and tangeretin are preferred. In the following chemical formula, R, $R_1$, $R_2$, $R_3$, and $R_4$ are OMe, OMe, H, Me, and OMe, respectively, in nobiletin, or OMe, H, H, Me, and OMe, respectively, in tangeretin (Me represents methyl group, OMe represents methoxy group, and H represents hydrogen).

The polymethoxyflavonoid may consist of a single kind of polymethoxyflavonoid, or a mixture of arbitrary two or more kinds of polymethoxyflavonoids.

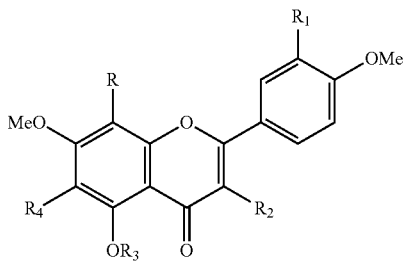

(In the formula, R, $R_1$, $R_2$, and $R_4$ independently represent hydrogen atom or methoxy group, and $R_3$ represents hydrogen atom or methyl group.)

The polymethoxyflavonoid may be extracted from a fruit, leaf, root, stem etc. of a *Citrus* species or another plant containing that substance, or may be produced by chemical synthesis. As nobiletin and tangeretin obtained by chemical synthesis, commercial synthetic products (for example, those produced by Tokyo Chemical Industry), and so forth can be used.

The extract of *Citrus depressa* can be produced by, for example, extraction of fruit and/or leaf of *Citrus depressa* with water and/or an organic solvent. The organic solvent may contain water. *Citrus depressa* (Shiikuwasha) is a kind of *Citrus* species belonging to the family Rutaceae.

The fruit and/or leaf may be the whole fruit and/or leaf, or may be a part thereof. For example, the fruit may be pulp or pericarp. Further, the fruit and/or leaf may be used as they are, or may be used after crushing. Further, the fruit and/or leaf may be a juice extraction residue of a fruit and/or leaf, or a part thereof. Hereafter, these fruit and/or leaf, a part thereof, crushed product thereof, and juice extraction residue thereof may be referred to as "*Citrus depressa* fruit and/or leaf etc."

Examples of the organic solvent include methanol, ethanol, propanol, butanol, ethyl acetate, acetone, hexane, chloroform, diethyl ether, these organic solvents containing water, combination of each of these organic solvents and these organic solvents containing water, but among these, ethanol is preferred. Although water content in the organic solvent is not particularly limited, it is preferably 0 to 90 mass %, more preferably 0 to 40 mass %.

Although amount of the organic solvent with respect to the *Citrus depressa* fruit and/or leaf etc. used in the extraction with the organic solvent is not particularly limited, ratio (weight ratio) of the *Citrus depressa* fruit and/or leaf etc.: organic solvent is preferably 1:1 to 1:100, more preferably 1:1 to 1:20.

Although the method of the extraction is not particularly limited, examples include, for example, a method of adding an organic solvent to *Citrus depressa* fruit and/or leaf etc., performing extraction preferably for 5 minutes to 3 hours, and then collecting the liquid phase by a solid/liquid separation means such as filtration or centrifugal separation.

Further, after the extraction or before drying process, it is preferable to add a clathrating agent for making the polymethoxyflavonoid water-soluble. If such a clathrating agent is used, effects of improving water solubility, digestion and absorption, and flavor of the polymethoxyflavonoid can be expected. As the clathrating agent, it is preferable to use a compound for clathrate such as cyclodextrin. In the case of cyclodextrin, amount of the clathrating agent is preferably 0.1 to 95 mass %, preferably 1 to 90 mass %, based on the total mass of the solid matter of the extract of *Citrus depressa* and cyclodextrin.

The extract of *Citrus depressa* of the present invention can also be produced by supercritical extraction. Specifically, it can be produced by, for example, subjecting frozen and crushed *Citrus depressa* fruit or leaf, or *Citrus depressa* fruit or leaf powdered by lyophilization or hot air-drying to supercritical extraction performed under the following conditions (a) to (d).
(a) Extraction solvent is carbon dioxide (carbon dioxide gas).
(b) Extraction temperature is 25 to 120° C.
(c) Pressure is 5.5 to 60 MPa.
(d) Extraction time is 5 to 70 minutes.

As the extraction fluid, it is possible to use supercritical propane, supercritical ethylene, supercritical 1,1,1,2-tetrafluoroethane, or the like, in order to improve extraction efficiency of the *Citrus depressa* fruit or leaf. However, in order to increase safety as food or drink, it is preferable to use carbon dioxide (carbon dioxide gas). The extraction temperature may be appropriately chosen to be in the temperature range of 31.1 to 120° C., but in order to improve the extraction efficiency and increase the content of the polymethoxyflavonoid, especially nobiletin and/or tangeretin, it is preferably in the range of 40 to 80° C., more preferably in the range of 60 to 80° C. The pressure is preferably in the range of 5.5 to 60 MPa, more preferably in the range of 20 to 40 MPa. Further, in the present invention, ethanol, water, or the like may be used as an entrainer, in order to improve the extraction efficiency. Although the extraction time may be appropriately chosen according to the temperature or pressure, it is, for example, preferably in the range of 10 to 50 minutes, more preferably 20 to 30 minutes.

The extraction operation can be performed by using a commercially available apparatus.

The extract of *Citrus depressa* of the present invention can also be produced by subcritical extraction. Specifically, it can be produced by, for example, subjecting frozen and crushed *Citrus depressa* fruit or leaf, or *Citrus depressa* fruit or leaf powdered by lyophilization or hot air-drying to subcritical extraction performed under the following conditions (a) to (d).

(a) Extraction solvent is water.
(b) Extraction temperature is 140 to 200° C.
(c) Pressure is 3 to 15 MPa.
(d) Extraction time is 0 to 10 minutes.

The extraction time of 0 minute means that immediately after the temperature is raised to the objective extraction temperature from the start of the extraction, the temperature is lowered by cooling to the level at the start of the extraction.

Examples of the extraction fluid used for the subcritical extraction include, for example, water and carbon dioxide. However, in order to increase safety as food or drink, it is preferable to use water.

In the case of using water as the extraction fluid, the extraction temperature may be appropriately chosen to be in the temperature range of 140 to 200° C., but in order to improve the extraction efficiency and increase the content of the polymethoxyflavonoid, especially nobiletin and/or tangeretin, it is preferably in the range of 140 to 180° C. The pressure is preferably in the range of 3 to 15 MPa in the case of using water as the extraction fluid.

Although the extraction time may be appropriately chosen according to the temperature or pressure, it is preferably in the range of 0 to 10 minutes, more preferably 0 to 5 minutes.

The extraction operation can be performed by using a commercially available apparatus.

Yields of nobiletin and tangeretin in an extract obtained as described above by the extraction method using water, an organic solvent, or an organic solvent containing water, supercritical extraction, or subcritical extraction are usually about 0.001 to 3 mass %, and 0.0001 to 2 mass %, respectively, based on the weight of *Citrus depressa* fruit and/or leaf etc.

The extract of *Citrus depressa* obtained as described above contains preferably 0.3 mass % or more, more preferably 0.6 mass % or more, still more preferably 1 mass % or more, further preferably 3 mass % or more, particularly preferably 10 mass % or more, of the polymethoxyflavonoid in terms of solid matter. Further, such a extract of *Citrus depressa* contains preferably 0.2 mass % or more, more preferably 0.4 mass % or more, still more preferably 2 mass % or more, particularly preferably 5 mass % or more, of nobiletin, and/or preferably 0.1 mass % or more, more preferably 0.2 mass % or more, still more preferably 1 mass % or more, particularly preferably 2 mass % or more, of tangeretin, in terms of solid matter. The phrase "in terms of solid matter" has the same meaning as "amount as solid matter (solid content)". Further, expression that a drug, food or the like contains X % or more of the extract of *Citrus depressa*, polymethoxyflavonoid, nobiletin, or tangeretin "in terms of solid matter" means that the ratio of the amount of the solid matter of the extract of *Citrus depressa*, polymethoxyflavonoid, nobiletin, or tangeretin to the amount of the solid matter of the drug, food or the like is X %.

The extract may be used as it is, or may be used after concentration, and the solvent may be partially or completely removed. The concentration or removal of the solvent can be carried out by such methods as various chromatography techniques, distillation, solidification by drying, and recrystallization. In particular, organic solvents not preferred to be contained in a drug or food or drink, for example, methanol, propanol, butanol, ethyl acetate, acetone, hexane, chloroform, diethyl ether, etc., is preferably removed. Further, in order to increase the content of the polymethoxyflavonoid, especially nobiletin and/or tangeretin, the extract may be fractionated. The content of the polymethoxyflavonoid such as nobiletin and/or tangeretin can be measured by HPLC or the like.

Such an extract of *Citrus depressa* or polymethoxyflavonoid as described above can be used as it is as an active ingredient of the muscle atrophy inhibitor (henceforth also referred to as "agent of the present invention"), food, drink, or feed. The extract of *Citrus depressa* or polymethoxyflavonoid may be in the form of a solution, or it may be lyophilized or spray-dried in a conventional manner, then stored and used as powder.

The agent of the present invention can be used as a drug or an active ingredient thereof as one embodiment. As the agent of the present invention, an extract of *Citrus depressa* or polymethoxyflavonoid can be orally administered as it is or as a combination with a pharmaceutically acceptable carrier to a mammal including human.

Preparation form of the agent of the present invention is not particularly limited, and examples include tablets (including sugar-coated tablets, enteric coated tablets, and buccal tablets), powders, capsules (including enteric capsules and soft capsules), granules (including coated granules), pills, troches, enclosed liposome agents, solutions, pharmaceutically acceptable sustained release preparations of these, and so forth. When the preparation is prepared, additives commonly used in usual oral drugs as pharmaceutical ingredients, such as carrier, excipient, binder, disintegrating agent, lubricant, stabilizer, flavoring agent, diluent, surfactant and solvent, can be used. Further, so long as the effect of the present invention is not degraded, the extract of *Citrus depressa* or polymethoxyflavonoid may be used together with an agent or pharmaceutical composition having a muscle atrophy inhibition action, which is already known or will be found in future. The pharmaceutical composition used together may be contained in the agent of the present invention as one of active ingredients, or may not be contained in the agent of the present invention, but combined as a separate drug with the agent of the present invention to form a commercial product.

Examples of the carrier and excipient used for the aforementioned preparation include lactose, glucose, sucrose, mannitol, potato starch, corn starch, calcium carbonate, calcium phosphate, calcium sulfate, crystalline cellulose, glycyrrhizae radix pulverata, gentianae radix pulverata, and so forth, and examples of the binder include, for example, starch, gelatin, syrup, polyvinyl alcohol, polyvinyl ether, polyvinylpyrrolidone, hydroxypropylcellulose, ethylcellulose, methylcellulose, carboxymethylcellulose, and so forth.

Examples of the disintegrating agent include starch, agar, gelatin powder, sodium carboxymethylcellulose, calcium carboxymethylcellulose, crystalline cellulose, calcium carbonate, sodium hydrogencarbonate, sodium arginate, and so forth.

Examples of the lubricant include magnesium stearate, hydrogenated vegetable oil, Macrogol, and so forth, and examples of the colorant include Red No. 2, Yellow No. 4, Blue No. 1, which are allowed to be added to drugs, and so forth.

Tablets and granules can be coated with sucrose, hydroxypropylcellulose, purified shellac, gelatin, sorbitol, glycerol, ethylcellulose, hydroxypropylcellulose, hydroxypropylmethylcellulose, polyvinylpyrrolidone, cellulose acetate phthalate, hydroxypropylmethylcellulose phthalate, methyl methacrylate, methacrylic acid polymer, and so forth, as required.

One aspect of the present invention is use of an extract of *Citrus depressa* or polymethoxyflavonoid in preparation of a drug for inhibiting muscle atrophy. Another aspect of the present invention is an extract of *Citrus depressa* or polymethoxyflavonoid to be used for inhibiting muscle atrophy. Still another aspect of the present invention is a method for inhibiting muscle atrophy comprising administering an extract of *Citrus depressa* or polymethoxyflavonoid to a mammal.

Although amount of the extract of *Citrus depressa* or polymethoxyflavonoid contained in the agent of the present invention is not particularly limited and can be appropriately chosen, when an extract of *Citrus depressa* is used, for example, the amount is preferably 1 mass % or more, more preferably 10 mass % or more, in terms of the amount of the solid matter contained in the extract of *Citrus depressa*. Alternatively, the amount of the extract of *Citrus depressa* contained in the agent of the present invention is preferably 0.3 mass % or more, more preferably 0.6 mass % or more, further preferably 3.0 mass % or more, particularly preferably 10 mass % or more, in terms of polymethoxyflavonoid content. Although the maximum content of the extract of *Citrus depressa* is not particularly limited, it may be, for example, 95 mass % or less, 90 mass % or less, or 50 mass % or less, in terms of the amount of the solid matter in the extract of *Citrus depressa*, or it may be, for example, 95 mass % or less, 80 mass % or less, 60 mass % or less, or 40 mass % or less, in terms of the amount of polymethoxyflavonoid.

Further, when the polymethoxyflavonoid is used, the amount of polymethoxyflavonoid contained in the agent may be 0.001 mass % or more, preferably 0.1 mass % or more, more preferably 0.3 mass % or more, further preferably 0.6 mass % or more, still further preferably 3.0 mass % or more, particularly preferably 10 mass % or more, in terms of solid matter. Although the maximum content of the polymethoxyflavonoid is not particularly limited, it may be, for example, 95 mass % or less, 70 mass % or less, 60 mass % or less, 50 mass % or less, or 40 mass % or less.

When nobiletin is used as the polymethoxyflavonoid, the amount of nobiletin contained in the agent may be 0.0007 mass % or more, preferably 0.07 mass % or more, still more preferably 0.2 mass % or more, further preferably 0.4 mass % or more, still further preferably 2.0 mass % or more, particularly preferably 5 mass % or more, in terms of solid matter. Although the maximum content of nobiletin is not particularly limited, it may be, for example, 95 mass % or less, 70 mass % or less, 50 mass % or less, 30 mass % or less, or 10 mass % or less.

When tangeretin is used as the polymethoxyflavonoid, the amount of tangeretin contained in the agent may be 0.0004 mass % or more, preferably 0.04 mass % or more, still more preferably 0.1 mass % or more, further preferably 0.2 mass % or more, still further preferably 1.0 mass % or more, particularly preferably 2 mass % or more, in terms of solid matter. Although the maximum content of tangeretin is not particularly limited, it may be, for example, 95 mass % or less, 70 mass % or less, 50 mass % or less, 30 mass % or less, or 10 mass % or less.

When two or more kinds of polymethoxyflavonoids, such as nobiletin, tangeretin, and other polymethoxyflavonoids, are used, the content thereof in the agent may be appropriately chosen to be within the aforementioned ranges.

The agent of the present invention is useful for prophylactic and therapeutic treatments of muscle atrophy, for example, muscle atrophy resulting from aging, bedridden, sedentary lifestyle, or spaceflight; muscle atrophy resulting from immobilization of limbs performed for treatment of injury etc., or postoperative rest; muscle atrophy resulting from side reactions of drugs such as steroids; and muscle atrophy resulting from paralysis, spinal cord injury, traumatic injury of peripheral nerve, osteoarthritis, rheumatoid arthritis, diabetes, thermal burn, polio, Guillain-Barre syndrome, muscular dystrophy, congenital myotonia, infectious disease accompanied by inflammation such as AIDS and viral hepatitis, sepsis accompanying infectious disease, inflammatory bowel disease, connective tissue disease, renal failure, hepatic failure, cardiac failure, cancer, malignant tumor, cachexia, anorexia or hypercatabolism in terminal symptoms of a disease, and so forth; reduction of muscle force resulting from muscle atrophy; and amyotrophic lateral sclerosis and recovery of activities of daily living (ADL) at the time of rehabilitation. Further, the prophylactic and therapeutic treatments of muscle atrophy include suppressing expression of a muscle atrophy-related gene (atrogene) and/or a gene that participates in suppression of muscle growth. Examples of the muscle atrophy-related gene include MuRF1 (Nikawa, T. et al., The FASEB Journal express article 10.1096/fj.03-0419fje. Published online, Jan. 8, 2004), and atrogin-1 (Gomes, M. D. et al., PNAS, 98(25), 2001), and examples of the gene that participates in suppression of muscle growth include myostatin (also called growth/differentiation factor 8) gene.

Time for administration of the agent of the present invention is not particularly limited, and can be appropriately chosen according to a state of an object of the administration.

Dose of the agent of the present invention is appropriately chosen depending on age, sex, state of the object of administration, other conditions, and so forth. The dose is preferably chosen to be in the range of 1 to 250 mg/kg/day as a standard in terms of the amount of the solid matter contained in the extract of *Citrus depressa*.

The agent can be administered at a dose of preferably 0.03 mg/kg/day or more, more preferably 0.3 mg/kg/day or more, further preferably 3 mg/kg/day or more, particularly preferably 30 mg/kg/day or more, as a standard in terms of the amount of polymethoxyflavonoid contained in the solid matter of the extract of *Citrus depressa*. In this case, the maximum dose may be 150 mg/kg/day or less, preferably 120 mg/kg/day or less, more preferably 90 mg/kg/day or less, particularly preferably 60 mg/kg/day or less.

The dose of the agent of the present invention in terms of the amount of polymethoxyflavonoid may be preferably 0.03 mg/kg/day or more, more preferably 0.3 mg/kg/day or more, further preferably 3 mg/kg/day or more, particularly preferably 30 mg/kg/day or more, as a standard. The maximum dose in this case may be 150 mg/kg/day or less, preferably 120 mg/kg/day or less, more preferably 90 mg/kg/day or less, particularly preferably 60 mg/kg/day or less.

The dose in terms of the amount of nobiletin is preferably 0.02 mg/kg/day or more, more preferably 0.2 mg/kg/day or more, further preferably 2 mg/kg/day or more, particularly preferably 20 mg/kg/day or more, as a standard. The maximum dose in this case may be 90 mg/kg/day or less, preferably 72 mg/kg/day or less, more preferably 54 mg/kg/day or less, particularly preferably 36 mg/kg/day or less.

The dose in terms of the amount of tangeretin may be preferably 0.01 mg/kg/day or more, more preferably 0.1 mg/kg/day or more, further preferably 1 mg/kg/day or more, particularly preferably 10 mg/kg/day or more, as a standard. The maximum dose in this case may be 60 mg/kg/day or less, preferably 48 mg/kg/day or less, more preferably 36 mg/kg/day or less, particularly preferably 24 mg/kg/day or less.

When the administration period is long, for example, one to several months or longer, the effect can be expected even with a dose of the agent of about 1/10 to 1/100 of the aforementioned ranges.

Regardless of the administration period, the daily dose of the agent can be administered one time a day, or two or more times a day as divided portions.

The agent of the present invention, or the extract of *Citrus depressa* or polymethoxyflavonoid as the active ingredient of the agent may be added to diets (drink or food).

Further, it is also possible to add the extract of *Citrus depressa*, the polymethoxyflavonoid, or the agent of the present invention to a drink or food as an active ingredient to produce a drink or food having a muscle atrophy inhibition action as one embodiment of the muscle atrophy inhibitor.

Forms and properties of the food and drink are not particularly limited so long as the effect of the extract of *Citrus depressa* or the polymethoxyflavonoid is not degraded, and they can be orally ingested, and they can be prepared by using usual raw materials used for foods and drinks and usual methods, except that the extract of *Citrus depressa* or the like is added.

Forms of such foods as mentioned above are not particularly limited, and they may be in the form of liquid, paste, gellated solid, powder, or the like. Examples include, for example, tablet confectioneries, and liquid diets, as well as, for example, flour products such as bread, macaroni, spaghetti, noodles, cake mix, fry powder and bread crumbs; ready-to-eat foods such as instant noodles, pot noodles, retort and cooked foods, canned cooking, foods for microwave heating, instant soup and stew, instant miso soup and Japanese clear soup, canned soup, freeze-dried foods, and other ready-to-eat foods; processed agricultural products such as canned agricultural products, canned fruits, jams and marmalades, pickles, cooked beans, dry agricultural products, and cereals (processed grain products); processed marine products such as canned marine products, fish ham and sausages, seafood paste products, marine dainties, and tsukudani (marine products boiled in soy source; processed livestock products such as canned livestock products and pastes, and livestock meat ham and sausages; milks and dairy products such as processed milk, milk drinks, yoghurts, lactic acid drinks, cheese, ice creams, modified milk powders, creams, and other dairy products; oils and fats such as butter, margarines, and vegetable oils; basic seasoning such as soy sauce, miso, sauces, processed tomato seasoning, mirin, and vinegars; complex seasonings and foods such as cooking mix, curry powder or roux, sauces for dipping, dressings, noodle soups, spices, and other complex seasonings; frozen foods such as frozen food materials, semi-cooked frozen foods, and cooked frozen foods; confectioneries such as caramel candies, candies, chewing gums, chocolates, cookies, biscuits, cakes, pies, snacks, crackers, Japanese sweets, rice confectioneries, bean confectioneries, dessert pastries, jellies, and other confectioneries; beverages such as carbonated drinks, natural fruit juices, fruit juice drinks, fruit juice soft drinks, fruit pulp drinks, fruit drinks with fruit pulp, vegetable based drinks, soy milk, soy milk drinks, coffee drinks, tea drinks, powdered drinks, concentrated drinks, sports drinks, nutritional beverage, alcoholic drinks, and other beverages; other commercial foods such as baby foods, rice seasonings, and seaweed seasonings for boiled rice soaked with tea; modified milk powder for infants; enteral nutrients; functional foods (foods for specified health use, foods with nutrient function claims), and so forth.

Furthermore, by adding the extract of *Citrus depressa*, the polymethoxyflavonoid, or the agent of the present invention to a feed as an active ingredient, a feed having a muscle atrophy inhibition action can be prepared, as one embodiment of the muscle atrophy inhibitor.

Form of the feed is not particularly limited. For example, the feed can be prepared by blending cereals such as corn, wheat, barley, rye and milo; vegetable oil meals such as soybean oil meal, rapeseed oil meal, coconut oil meal and linseed oil meal; brans such as wheat bran, rice bran, and defatted rice bran; production meals such as cone gluten meal and corn jam meal; animal or fish-derived feeds such as fish meal, skim milk powder, whey, yellow grease and tallow; yeasts such as torula yeast and brewer's yeast; mineral material feeds such as tribasic calcium phosphate and calcium carbonate; oils and fats; monomeric amino acids; saccharides, and so forth. Examples of the form of the feed include, for example, pet food, livestock feed, fish breeding feed, and so forth.

The amount of the extract of *Citrus depressa* or polymethoxyflavonoid contained in the food or drink (including feed) of the present invention is not particularly limited, and may be appropriately chosen. However, for example, when a extract of *Citrus depressa* is used, the amount thereof is preferably 1 mass % or more in terms of the amount of solid matter contained in the extract of *Citrus depressa*. Alternatively, the amount of the extract of *Citrus depressa* contained in the food or drink may be 0.3 mass % or more, preferably 0.6 mass % or more, further preferably 3 mass % or more, particularly preferably 10 mass % or more, in terms of polymethoxyflavonoid content. Although the maximum content of the extract of *Citrus depressa* is not particularly limited, it may be, for example, 95 mass % or less, 50 mass % or less, 30 mass % or less, 20 mass % or less, or 10 mass % or less, in terms of the amount of solid matter in the extract of *Citrus depressa*, or it may be, for example, 95 mass % or less, 70 mass % or less, 60 mass % or less, 50 mass % or less, or 40 mass % or less, in terms of the amount of polymethoxyflavonoid.

Further, when the polymethoxyflavonoid is used, the amount of polymethoxyflavonoid contained in the food or drink is preferably 0.3 mass % or more, more preferably 0.6 mass % or more, still more preferably 3.0 mass % or more, particularly preferably 10 mass % or more, in terms of solid matter. Although the maximum content of the polymethoxyflavonoid is not particularly limited, it may be, for example, 95 mass % or less, 70 mass % or less, 60 mass % or less, 50 mass % or less, or 40 mass % or less.

When nobiletin is used, the amount of nobiletin contained in the food or drink is preferably 0.2 mass % or more, more preferably 0.4 mass % or more, still more preferably 2.0 mass % or more, particularly preferably 5 mass % or more, in terms of solid matter. Although the maximum content of nobiletin is not particularly limited, it may be, for example, 95 mass % or less, 70 mass % or less, 50 mass % or less, 30 mass % or less, or 10 mass % or less.

When tangeretin is used, the amount of tangeretin contained in the food or drink is preferably 0.1 mass % or more, more preferably 0.2 mass % or more, still more preferably 1.0 mass % or more, particularly preferably 2 mass % or more, in terms of solid matter. Although the maximum content of tangeretin is not particularly limited, it may be, for example, 95 mass % or less, 70 mass % or less, 50 mass % or less, 30 mass % or less, or 10 mass % or less.

Further, the food or drink (including feed) of the present invention desirably contains 5 mg or more, preferably 18 mg or more, more preferably 180 mg or more, of the extract of *Citrus depressa* in terms of solid matter in an amount for single ingestion.

Further, the food or drink (including feed) of the present invention desirably contains 1.8 mg or more, preferably 18 mg or more, more preferably 180 mg or more, of the polymethoxyflavonoid in terms of solid matter in an amount for single ingestion.

Further, the food or drink (including feed) of the present invention desirably contains 1.2 mg or more, preferably 12 mg or more, more preferably 120 mg or more, of nobiletin in terms of solid matter in an amount for single ingestion.

Further, the food or drink (including feed) of the present invention desirably contains 0.6 mg or more, preferably 6 mg or more, more preferably 60 mg or more, of tangeretin in terms of solid matter in an amount for single ingestion.

EXAMPLES

Hereafter, the present invention will be more specifically explained with reference to examples. However, the present invention is not limited to these examples.

Example 1

Muscle atrophy inhibition effects of extract of *Citrus depressa*, polymethoxyflavonoid, nobiletin, and tangeretin were evaluated in a glucocorticoid-induced rat muscle atrophy model.

The extract of *Citrus depressa* used (commercial product, ARKRAY) was obtained by adding cyclodextrin as a clathrating agent to an extract from squeezed residue of *Citrus depressa* fruits with water-containing ethanol, and had the following composition according to the usual specification thereof.

| | |
|---|---|
| Solid matter | 92 mass % or more |
| Cyclodextrin | 50 mass % |
| Polymethoxyflavonoids | 10 mass % or more |

Nobiletin content and tangeretin content of the extract of *Citrus depressa* (containing cyclodextrin) used for the following experiment were 6.9 to 8.5 mass % and 3.4 to 4.1 mass %, respectively.

As the glucocorticoid for preparing the muscle atrophy model, dexamethasone was used.

Male SD rats (15-month old) were preliminarily fed for one week, and divided into three groups (dexamethasone non-administration group (CTL), dexamethasone administration group (DEX), and dexamethasone and extract of *Citrus depressa* (Shiikuwasha extract) administration group (SE), n=6 for the DEX and CTL groups, n=5 for the SE group).

Then, the rats of the DEX group and the CTL group were fed with standard feed AIN-93M (CLEA Japan), and the rats of the SE group were fed with AIN-93M added with the extract of *Citrus depressa* at a ratio of 1 mass %, for two weeks.

After two-week feeding, the rats of the DEX group and SE group were intraperitoneally administered with 750 µg/kg body weight of dexamethasone once a day for 5 days to induce muscle atrophy. The rats of the CTL group were intraperitoneally administered with physiological saline once a day for 5 days.

On the 6th day from the start of the administration of dexamethasone, the rats were dissected, the left hindlimb tibialis anterior muscles were collected, and wet weights of the muscles were measured. The muscle atrophy inhibition effect was evaluated according to differences in weights of the muscles of the groups.

As shown in Table 1, the tibialis anterior muscle weight of the dexamethasone administration group (DEX) significantly and markedly decreased to about 78.7% of that of the dexamethasone non-administration group (CTL), and thus it was confirmed that the muscles were atrophied by administration of dexamethasone. Further, the muscle weight of the dexamethasone and extract of *Citrus depressa* (shiikuwasha extract) administration group (SE) fed with the feed containing the extract of *Citrus depressa* was significantly larger than that of the DEX group (about 92.3% of that of the CTL group, p<0.05, statistically significant difference over the DEX group according to the Dunnett test), and thus it was confirmed that the muscle atrophy was inhibited by the extract of *Citrus depressa*.

TABLE 1

| | CTL | DEX | SE |
|---|---|---|---|
| Wet muscle weight (g) | 1.187 | 0.934 | 1.096 |
| SD | 0.123 | 0.111 | 0.094 |

Example 2

The tibialis anterior muscles collected in Example 1 mentioned above were used to evaluate expression amounts of genes that participate in muscle atrophy.

The tibialis anterior muscle was frozen in liquid nitrogen immediately after the collection, and homogenized in Trizol Reagent (Invitrogen), and the total RNA was extracted by using RNeasy Mini Kit (QIAGEN). cDNA was obtained by the total RNA by using High Capacity cDNA Reverse Kit (ABI). The cDNA, primers for amplifying each of the atrogin-1, MuRF1, and myostatin genes (ABI), and Taqman Fast Universal PCR Master Mix (ABI) were mixed, and expression amount of each gene in the test sample was relatively quantified by the real time PCR method, with taking the gene expression amount in the DEX group as 1. In statistical analysis, it was determined whether there were statistically significant differences between the values obtained for the DEX group and the values obtained for the other groups according to the Dunnett test.

It is known that muscle atrophy is accompanied by increased muscle protein degradation, in addition to reduction of muscle protein synthesis. The major protein degradation systems in skeletal muscles include three systems, ubiquitin-proteasome system, calpain system, and autophagy system, and it is considered that, among these, the ubiquitin-proteasome system plays an especially important role. Proteins are labeled by ubiquitin ligase, and the ubiquitinated proteins are degraded by proteasome. It is considered that by inhibiting the ubiquitin-proteasome pathway, protein degradation in muscle atrophy can be inhibited (Tawa, N. E. Jr., J. Clin. Invest., 100(1):197-203, 1997).

As muscle-specific ubiquitin ligases for which it has been to date elucidated that expression amount of the gene thereof increases at the time of muscle atrophy, there are known MuRF1 (Nikawa, T. et al., The FASEB Journal express article 10.1096/fj.03-0419fje, Published online Jan. 8, 2004), and atrogin-1 (Gomes, M. D. et al., PNAS, 98(25) 2001). Further, myostatin (also called as growth/differentiation factor 8) gene is also known as a repressor of muscle growth (McPherron, A. C. et al., Nature, 387:83-90, 1997).

The results of analysis of expression amounts of the genes performed by real-time PCR are shown in FIG. 1.

As for the gene expression amounts in the CTL group, the expression amounts of the atrogin-1 gene and the MuRF1 gene were 0.26±0.06 and 0.10±0.02, respectively, relative to the expression amounts in the DEX group, which were taken as 1.0, and thus it was confirmed that they were significantly increased by the administration of dexamethasone. In contrast, in the SE group, the expression amounts of the atrogin-1 gene and the MuRF1 gene were 0.73±0.12 ($p<0.01$) and 0.54±0.15 ($p<0.05$), respectively, which were both significantly reduced from those observed in the DEX group, and thus it was confirmed that the expression of the muscle atrophy-related genes was significantly inhibited by the ingestion of the extract of *Citrus depressa*.

Example 3

In Examples 1 and 2, 1 mass % of the extract of *Citrus depressa* was added to the feed, and fed. However, in this example, for individual evaluation of polymethoxyflavonoid, nobiletin (Tokyo Chemical Industry), and tangeretin (Tokyo Chemical Industry), they were each mixed with the feed at a ratio of 0.001 mass % for polymethoxyflavonoid (PMF group), 0.0007 mass % for nobiletin (NOB group), or 0.0004 mass % for tangeretin (TAN group), and fed for two weeks. Then, dexamethasone was administered to the animals of the groups to induce muscle atrophy. These groups were examined by comparison with the non-treatment group (CTL group) and the dexamethasone administration group (DEX group). As the polymethoxyflavonoid, a mixture of nobiletin and tangeretin at a ratio of 6.9:3.4 was used.

As for the animal species, SD rats of eight-month old were used, and the evaluation was performed with the same experimental method as that used in Examples 1 and 2. On the 6th day from the start of the administration of dexamethasone, the left hindlimb tibialis anterior muscles were collected from the rats.

Figure 2:
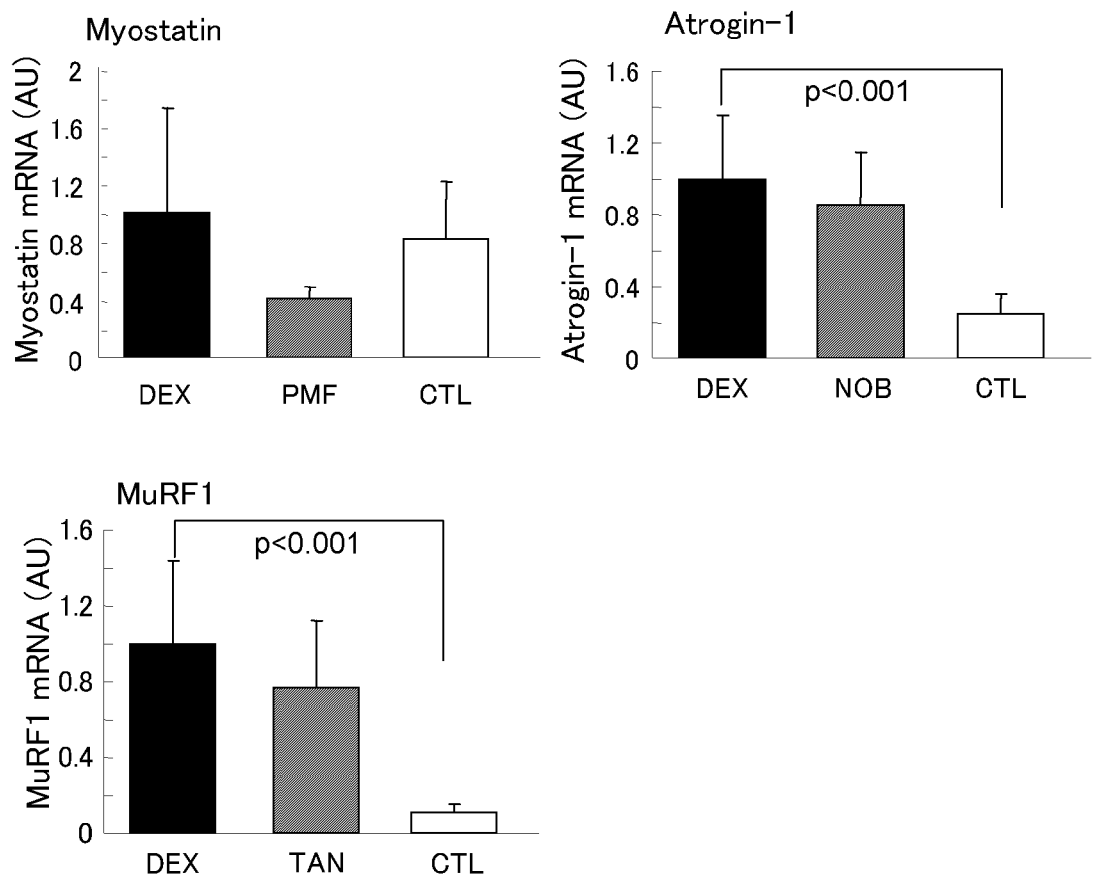

The results of evaluation of gene expression amounts performed in the same manner as that of Example 2 from tibialis anterior muscles are shown in FIG. 2. As for the gene expression amounts in the CTL group, the expression amounts of the atrogin-1 gene and the MuRF1 gene were 0.25±0.11 and 0.11±0.04, respectively, relative to the expression amounts observed in the DEX group, which were taken as 1.0, and thus it was confirmed that they were significantly increased by the administration of dexamethasone. The expression amount of the myostatin gene was 0.81±0.39, and increase of the expression amount of this gene was also confirmed. In contrast, in the PMF group, the expression amount of the myostatin gene was 0.40±0.08, and thus decrease of the expression amount was observed. In the NOB group, the expression amount of the atrogin-1 gene was 0.85±0.29, and thus decrease of the expression amount was observed. Also in the TAN group, the expression amount of the MuRF1 gene was 0.77±0.35, and thus decrease of the expression amount was observed.

Since the average daily Food intake of the rats used for the experiment was 20.1 g, the polymethoxyflavonoid ingestion amount in the PMF group was about 0.20 mg per day. Further, the daily food intake per body weight is calculated to be 0.339 mg/1 kg of body weight from the average body weight (592.7 g). Further, in the NOB group, the nobiletin ingestion amount was about 0.14 mg per day, and the daily ingestion amount per unit body weight was about 0.237 mg/1 kg of body weight. In the TAN group, the daily tangeretin ingestion amount was about 0.08 mg, and the daily ingestion amount per unit body weight was about 0.136 mg/1 kg of body weight. From these data, it is considered that ingestion amounts with which the effect can be expected are about 0.3 mg/kg/day for polymethoxyflavonoids, about 0.2 mg/kg/day for nobiletin, and about 0.1 mg/kg/day for tangeretin.

Further, if it is taken into consideration that the evaluation of this experiment was performed with a very short ingestion period of 19 days, it can be expected that, even with a smaller ingestion amount, the same effect can be obtained by continuous ingestion.

Example 4

Male SD rats (18-month old) were preliminarily fed for one week, and divided into three groups (control group (CTL), hindlimb immobilization group (FIX), and hindlimb immobilization and extract of *Citrus depressa* (shiikuwasha extract) administration group (SE), n=7 for the FIX and CTL groups, n=6 for the SE group).

Then, the rats of the FIX group and the CTL group were fed with the standard feed AIN-93M, and the rats of the SE group were fed with AIN-93M added with the extract of *Citrus depressa* at a ratio of 1 mass %, for two weeks.

After two-week feeding, both hindlimbs of the rats of the FIX group and SE group were immobilized with surgical cast for one week to induce muscle atrophy. Hindlimbs of the rats of the CTL group were not immobilized with surgical cast.

On the 8th day from the start of the immobilization of the hindlimbs with surgical cast, the rats were dissected, hindlimb soleus muscles were collected, and weights of the muscles were measured. In statistical analysis, it was determined whether there were statistically significant differences between the values obtained for the FIX group and the values obtained for the other groups according to the Dunnett test.

Figure 3:
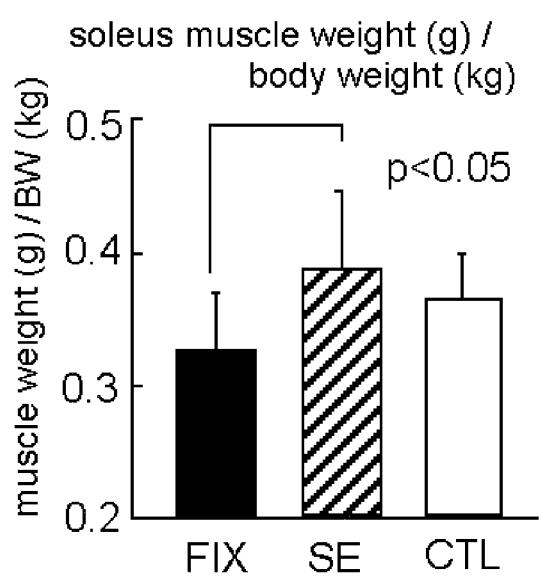
FIG. 3 is a graph showing suppression of reduction of soleus muscle weight in hindlimb-immobilized rats provided by administration of extract of *Citrus depressa*.
CTL: Non-treated group
FIX: Hindlimb immobilization group
SE: Hindlimb immobilization and extract of *Citrus depressa* (shiikuwasha extract) administration group

The results are shown in FIG. 3. Both the body weight and soleus muscle weight were decreased by immobilization of the hindlimbs with surgical cast. The soleus muscle weight per kg of body weight was 0.37±0.03 for the CTL group, whereas the same observe for the FIX group was 0.33±0.04, and thus decreased compared with that observed for the CTL group. However, in the SE group, the soleus muscle weight was 0.39±0.07, thus significantly increased compared with the FIX group ($p<0.05$), and increased to the same level as that of the CTL group or further higher level.

Example 5

Jelly Food

Among the raw materials mentioned below, nobiletin and cyclodextrin were used to prepare a solution of nobiletin clathrated with cyclodextrin, and this nobiletin solution and the other raw materials mentioned below were dissolved in water to prepare a jelly raw material dissolved solution. The solution was sterilized in a conventional manner, and filled in a cup in an amount of 100 g to prepare jelly food (100 g per piece) having the following composition in a conventional manner. The content of nobiletin in one piece of the obtained jelly food was 70 mg. It was revealed that results indicating muscle atrophy inhibition action could be obtained by ingesting two pieces per day of this food for a long period of time.

| | |
|---|---:|
| dextrin (Matsutani Chemical Industry) | 25.0 mass% |
| Whey protein (Morinaga Milk Industry) | 12.5 mass% |
| gelling agent (San-Ei Gen F.F.I.) | 0.3 mass% |
| citric acid (San-Ei Gen F.F.I.) | 0.2 mass% |
| ascorbate Na (DSM Nutrition) | 0.1 mass% |
| nobiletin (Tokyo Chemical Industry) | 0.07 mass % |
| cyclodextrin (San-Ei Gen F.F.I.) | 0.07 mass % |
| flavor (San-Ei Gen F.F.I.) | 0.02 mass% |
| vitamin D (San-Ei Gen F.F.I.) | $5.0 \times 10^{-7}$ mass % |
| water | 61.74 mass % |

Example 6

Drink

Among the raw materials mentioned below, tangeretin and cyclodextrin were used to prepare a solution of tangeretin clathrated with cyclodextrin, and this tangeretin solution and the other raw materials mentioned below were dissolved in water to prepare a drink raw material dissolved solution. The solution was filled in a bottle to prepare a drink (500 ml per bottle) having the following composition in a conventional manner. The content of tangeretin in the obtained drink contained in one container was 55.51 mg. It was revealed that results indicating muscle atrophy inhibition action could be obtained by ingesting two containers per day of this drink for a long period of time.

| | |
|---|---:|
| dextrin (Matsutani Chemical Industry) | 7.0 mass % |
| protein hydrolysate (Morinaga Milk Industry) | 0.5 mass % |
| citric acid (San-Ei Gen F.F.I.) | 0.2 mass % |
| ascorbate Na (DSM Nutrition) | 0.2 mass % |
| flavor (San-Ei Gen F.F.I.) | 0.02 mass % |
| sweetener (San-Ei Gen F.F.I.) | 0.01 mass % |
| tangeretin (Tokyo Chemical Industry) | 0.008 mass % |
| cyclodextrin (San-Ei Gen F.F.I.) | 0.008 mass % |
| water | 92.05 mass % |

Example 7

Tablet Confectionary

A mixture having the following composition was tableted in a conventional manner to produce tablet confectionaries having a weight of 250 mg per tablet. Content of the extract of *Citrus depressa* in 1 g of the obtained tablet confectionaries was 60 mg. Since the polymethoxyflavonoid content in the extract of *Citrus depressa* used as the raw material was 10% or higher, content of the polymethoxyflavonoid in 1 g of the tablet confectionaries was about 6 mg. It was revealed that results indicating muscle atrophy inhibition action could be obtained by ingesting 16 tablets per day of this food for a long period of time.

| | |
|---|---:|
| powder candy (Showa Sangyo) | 86.0 mass % |
| extract of *Citrus depressa* (Arkray) | 6.0 mass % |
| citric acid (San-Ei Gen F.F.I.) | 4.0 mass % |
| flavor (San-Ei Gen F.F.I.) | 2.0 mass % |
| emulsifier (Kao) | 2.0 mass % |

Example 8

Chewable Tablet

Chewable tablets having the following composition and weight of 250 mg per tablet were produced in a conventional manner. Content of the extract of *Citrus depressa* in 1 g of the obtained chewable tablets was 200 mg. Since the polymethoxyflavonoid content in the extract of *Citrus depressa* used as the raw material was 10% or higher, content of the polymethoxyflavonoid in 1 g of the chewable tablets was about 20 mg. It was revealed that results indicating muscle atrophy inhibition action could be obtained by ingesting 4 tablets per day of this food for a long period of time.

| | |
|---|---:|
| erythritol (Mitsubishi Chemical Foods) | 68.0 mass % |
| extract of *Citrus depressa* (Arkray) | 20.0 mass % |
| citric acid (San-Ei Gen F.F.I.) | 7.0 mass % |
| talc (San-Ei Gen F.F.I.) | 3.0 mass % |
| flavor (San-Ei Gen F.F.I.) | 2.0 mass % |

Example 9

Enteral Nutrient (Concentrate Liquid Diet)

Casein and hardly digestible dextrin were dissolved in warm water, then dextrin, a mineral mixture, a vitamin mixture, and nobiletin clathrated with cyclodextrin were mixed with the solution, an emulsifier and soybean oil were added to the mixture, and the mixture was homogenized. The mixture was sterilized and filled in a conventional manner to prepare an enteral nutrient having the following composition. The mineral mixture and vitamin mixture mentioned below were obtained by mixing the ingredients in the amounts shown in Table 2. Content of nobiletin in 1000 ml of the obtained enteral nutrient was 46 mg. It was revealed that results indicating muscle atrophy inhibition action could be obtained by ingesting 1000 ml per day of this food for a long period of time.

| | |
|---|---:|
| dextrin (Matsutani Chemical Industry) | 15.0 mass % |
| casein sodium (Morinaga Milk Industry) | 4.0 mass % |
| soybean oil (Taiyo Yushi) | 3.0 mass % |
| hardly digestible dextrin (Matsutani Chemical Industry) | 1.0 mass % |
| mineral mixture | 0.3 mass % |
| emulsifier (San-Ei Gen F.F.I.) | 0.05 mass % |
| vitamin mixture | 0.02 mass % |
| flavor (San-Ei Gen F.F.I.) | 0.01 mass % |
| nobiletin (Tokyo Chemical Industry) | 0.0046 mass % |
| cyclodextrin (San-Ei Gen F.F.I.) | 0.0046 mass % |
| water | 76.6108 mass % |

TABLE 2

| | (/1000 ml) |
|---|---|
| mineral mixture | |
| Na | 900 mg |
| K | 1500 mg |
| Ca | 750 mg |
| Mg | 380 mg |
| Fe | 11 mg |
| vitamin mixture | |
| β-carotene | 1800 μg |
| Vitamin D | 5 μg |
| α-tocopherol | 12 mg |
| vitamin B1 | 1.6 mg |
| vitamin B2 | 1.8 mg |
| vitamin B6 | 3 mg |
| vitamin B12 | 3 μg |
| vitamin C | 100 mg |

INDUSTRIAL APPLICABILITY

According to the present invention, a muscle atrophy inhibitor is provided. The muscle atrophy inhibitor of the present invention can be used as a drug. Further, since the muscle atrophy inhibitor of the present invention uses an ingredient contained in *Citrus depressa* as the active ingredient, it is highly safe, and can be used for foods, drinks, and so forth.

What is claimed is:

1. A method for inhibiting muscle atrophy in a human in need thereof comprising administering a therapeutically effective amount of an extract of *Citrus depressa* to said human in need thereof wherein said human in need thereof has muscle atrophy which is caused by paralysis, spinal cord injury, traumatic injury of the peripheral nerve, osteoarthritis, rheumatoid arthritis, diabetes, thermal burn, polio, Guillain Barre syndrome, muscular dystrophy, congenital myotonia, AIDS, sepsis accompanying infectious disease, inflammatory bowel disease, connective tissue disease, renal failure, cardiac failure, cancer, malignant tumor, cachexia, anorexia, hypercatabolism, or amyotrophic lateral sclerosis.

2. The method for inhibiting muscle atrophy of claim 1, wherein the extract of *Citrus depressa* comprises polymethoxyflavonoid.

3. The method for inhibiting muscle atrophy of claim 1, wherein the extract of *Citrus depressa* comprises 0.3 mass % or more of a polymethoxyflavonoid in terms of solid matter.

4. The method for inhibiting muscle atrophy of claim 1, wherein the extract of *Citrus depressa* comprises nobiletin and/or tangeretin.

5. The method for inhibiting muscle atrophy of claim 1, wherein the extract of *Citrus depressa* comprises 0.2 mass % or more of nobiletin and/or 0.1 mass % or more of tangeretin in terms of solid matter.

6. The method for inhibiting muscle atrophy of claim 1, wherein the administering of the therapeutically effective amount of the extract of *Citrus depressa* comprises administering an extract of *Citrus depressa* at a dose of 1 to 250 mg/kg/day in terms of the amount of the solid matter contained in the extract of *Citrus depressa*.

7. The method for inhibiting muscle atrophy of claim 1, wherein the extract of *Citrus depressa* is an organic solvent extract of a fruit and/or leaf of *Citrus depressa*.

8. The method for inhibiting muscle atrophy of claim 1, wherein the extract of *Citrus depressa* is a supercritical extract and/or subcritical extract of a fruit and/or leaf of *Citrus depressa*.

9. The method for inhibiting muscle atrophy of claim 7, wherein the organic solvent is an organic solvent selected from the group consisting of methanol, ethanol, propanol, butanol, ethyl acetate, acetone, hexane, chloroform, diethyl ether, and these organic solvents containing water.

10. The method for inhibiting muscle atrophy of claim 7, wherein the organic solvent is ethanol or water-containing ethanol.

11. The method for inhibiting muscle atrophy of claim 1, wherein the extract of *Citrus depressa* further comprises a clathrating agent for making the polymethoxyflavonoid water-soluble.

12. The method for inhibiting muscle atrophy of claim 11, wherein the clathrating agent is cyclodextrin, and content thereof is 0.1 to 95 mass % based on the total mass of solid matter of the extract of *Citrus depressa* and the cyclodextrin.

13. The method for inhibiting muscle atrophy of claim 1, wherein the administration of the extract of *Citrus depressa* comprises administering an extract of *Citrus depressa* at a dose of 0.02 to 0.237 mg/kg/day as a standard in terms of the amount of the nobiletin contained in the solid matter of the extract of *Citrus depressa*.

\* \* \* \* \*